United States Patent [19]

Nacy et al.

[11] Patent Number: 5,919,459
[45] Date of Patent: Jul. 6, 1999

[54] COMPOSITIONS AND METHODS FOR TREATING CANCER AND HYPERPROLIFERATIVE DISORDERS

[75] Inventors: Carol A. Nacy; John W. Holaday, both of Bethesda, Md.

[73] Assignee: EntreMed, Inc., Rockville, Md.

[21] Appl. No.: 08/467,101

[22] Filed: Jun. 6, 1995

Related U.S. Application Data

[63] Continuation of application No. 08/271,557, Jul. 7, 1994, abandoned, which is a continuation of application No. 08/068,717, May 27, 1993, abandoned.

[51] Int. Cl.$^6$ .......................... A61K 39/00; A61K 45/00; A61K 39/385; A61K 45/05
[52] U.S. Cl. .................... 424/192.1; 424/184.1; 424/277.1; 424/278.1; 424/85.1; 424/145.1; 424/85.2; 424/195.11; 424/198.1; 424/450; 424/85.6; 424/155.1; 514/12; 530/350
[58] Field of Search ............................. 424/85.1, 184.1, 424/278.1, 145.1, 85.7, 85.6, 195.19, 198.1, 155.1, 277.1, 450; 530/350.1; 514/12

[56] References Cited

U.S. PATENT DOCUMENTS

| | | |
|---|---|---|
| 4,094,971 | 6/1978 | Chedid et al. . |
| 4,677,064 | 6/1987 | Mark et al. ............................... 435/68 |
| 4,690,915 | 9/1987 | Rosenbert et al. ......................... 514/2 |
| 4,745,051 | 5/1988 | Smith et al. .............................. 435/68 |
| 4,777,242 | 10/1988 | Nelles .................................... 530/351 |
| 4,780,313 | 10/1988 | Koichiro et al. .......................... 424/88 |
| 4,806,352 | 2/1989 | Cantrell ..................................... 424/92 |
| 4,879,236 | 11/1989 | Smith et al. ............................. 435/235 |
| 4,895,835 | 1/1990 | Hasegawa .................................. 514/8 |
| 4,963,354 | 10/1990 | Shepard et al. . |
| 5,030,621 | 7/1991 | Bystryn . |
| 5,194,384 | 3/1993 | Bystryn . |
| 5,409,698 | 4/1995 | Anderson et al. . |
| 5,650,152 | 7/1997 | Anderson et al. . |
| 5,665,383 | 9/1997 | Grinstaff et al. . |
| 5,681,812 | 10/1997 | Coon et al. . |
| 5,733,876 | 3/1998 | O'Reilly et al. . |

FOREIGN PATENT DOCUMENTS

| | | |
|---|---|---|
| WO 89/05631 | 6/1989 | WIPO . |
| WO 90/04412 | 5/1990 | WIPO . |
| WO 93/25225 | 12/1993 | WIPO . |

OTHER PUBLICATIONS

Alving, C.R., et al., "Adjuvant Effects of Liposomes Containing Lipid A: Enhancement of Liposomal Antigen Presentation and Recruitment of Macrophages," *Infection and Immunity*, vol. 60, No. 6, pp. 2438–2444 (Jun. 1992).

Webb, N. R., et al., "Cell–surface Expression and Purification of Human CD4 Produced in Baculovirus–Infected Insect Cells," *Proc. Natl. Acad. Sci.*, vol. 86, pp. 7731–7735 (Oct. 1989).

Verma, J.N., et al. "Adjuvant Effects of Liposomes Containing Lipid A: Enhancement of Liposomal Antigen Presentation and Recruitment of Macrophages," *Infection and Immunity*, vol. 60, No. 6, pp. 2438–2444 (Jun. 1992).

Sachs, L. "Growth, Differentiation and the Reversal of Malignancy," *Scientific American*, Jan. 1986, pp. 40–47.

Liotta, L.A., "Cancer Cell Invasion and Metastasis," *Scientific American*, Feb. 1992, pp. 54–63.

Feldman, M. and Eisenbach, L., "What Makes a Tumor Cell Metastatic?", *Scientific American*, Nov. 1988, pp. 60–85.

Haranaka, K., et al., "Role of Lipid A in the Production of Tumor Necrosis Factor and Differences in Antitumor Activity Between Tumor Necrosis Factor and Lipopolysaccharide," *Tohoku J. exp. Med.*, 1984, pp. 385–396.

Costa, A., "Breast Cancer Chemoprevention," *Eur J Cancer*, vol. 29A No. 4, pp. 589–592 (1993).

Efferth, T. and Volm, M., "Antibody–Directed Therapy of Multidrug–Resistant Tumor Cells," *Med. Oncol. & Tumor Pharmacother*, vol. 9 No. 1, pp. 11–19 (1992).

Asano, T. and Kleinerman, E., "Liposome–Encapsulated MTP–PE: A Novel Biologic Agent for Cancer Therapy," *Journal of Immunotherapy*, 14: pp. 286–292 (1993).

Bartlett, G.R., "Phosphorus Assay in Column Chromatography", *Scripps Clinic and Research Foundation*, vol. 234, No. 3, pp. 466–468 (1959).

New, R.C., "Liposomes A Practical Approach", *Practical Approach Series*, pp. 105–107 (1990).

White, W.I. et al., "Antibody and Cytotoxic T–lymphocyte Responses to a Single Liposome–Associated Peptide Antigen", *Vaccine*, vol. 13, No. 12, pp. 1111–1122 (1995).

Fan, D. et al., "Antiproliferative Activity of Liposome–Encapsulated Transforming Growth Factor–β against MDA–MB–435 Human Breast Carcinoma Cells", *Cancer Communications*, vol. 1, No. 6, pp. 337–343 (1989).

(List continued on next page.)

*Primary Examiner*—Nita Minnifield
*Attorney, Agent, or Firm*—Jones & Askew, LLP

[57] ABSTRACT

The present invention encompasses methods for reducing or inhibiting growth factor in cancer cells and tissues. More particularly immunogenic growth factor-containing compositions are administered to a human or animal with a cancer or tumor. The immunogenic compositions elicit the production of antibodies specific for growth factor which reduce the level of circulating growth factor, thus reducing or eliminating the proliferation of cancer. The present invention encompasses growth factor-containing liposomes and vesicles having portions of growth factor externally presented on their surfaces. The present invention also includes antibodies specific for growth factor. Thus, according to the present invention, growth factor levels are reduced either by active immunization of an individual using immunogenic growth factor-containing compositions or by passive immunization via administering to the individual an antibody or a group of antibodies specific for growth factor.

35 Claims, No Drawings

OTHER PUBLICATIONS

Youichi, Ishii et al., "Preparation of EGF Labeled Liposomes and Their Uptake by Hepatocytes", *Biochemical and Biophysical Research Communications,* vol. 160, No. 2, pp. 732–736 (1989).

Welch, Clin. Exp. Metastasis 15:272–306, 1997.

Mortarini et al. 1990 Int. J. Cancer 45: 334–41.

Munker et al. 1987 Cancer Res. 47: 4081–85.

Tubiana 1991. J. Cancer Res. Clin. Oncol. 117: 275–89.

Siemann© 1987 In: Rodent Tumor Models in Exptal Cancer Therapy ed: Kallman pp. 12–15; Pergamon Press, NY.

Langer. 1990. Science 249: 1527–1533.

Bennett et al. 1992. J. Immunol Methods 153: 31–40.

Byars et al 1987 Vaccine 5: 223.

Warren et al 1988. CRC Critical Rev. in Immunol. 8(2):83–101.

Asano et al 1993. J. Immunotherap. 14:286–92.

Ozen. 1992 Current Opin. Oncol. 4/3:435–441.

Rose 1991. Sem. in Oncol. 18(6):536–542.

Breitmeyer et al 1990 Surg. Clin. North Am. 70/5:1081–1102.

Kohn et al 1993. Int. J. Cancer. 53:968–972.

Webb et al. 1989. Cell–surface expression and purification of human CD4 produced in baculovirus . . . PNAS 86: 7731–35.

COMPOSITIONS AND METHODS FOR TREATING CANCER AND HYPERPROLIFERATIVE DISORDERS

This is a continuation of application Ser. No. 08/271,557 filed Jul. 7, 1994, now abandoned, which is a continuation of application Ser. No. 08/068,717 filed May 27, 1993, now abandoned.

TECHNICAL FIELD

The present invention relates to vaccines for preventing or reducing cancers expand in humans or animals. More particularly, the present invention relates to immunogenic compositions comprising growth factors, antibodies specific for growth factors, and methods of use thereof.

BACKGROUND OF THE INVENTION

While many cancers are treatable by chemotherapeutic agents, a significant number of cancers are intrinsically drug resistant and others acquire resistance during or following chemotherapy. Cancers frequently are resistant to more than one type of drug. This phenomenon is called multidrug resistance or MDR. Consequently, there is a great need for compositions and methods that can be used in addition to, or as alternatives to, chemotherapy for the treatment of cancer.

A major clinical problem of cancer is metastasis. By the time that the primary tumor is identified and localized, seed cells often have escaped and migrated or metastasized to other organs in the body where they establish secondary tumors. Surgical procedures are rarely sufficient to cure a cancer because even after the primary tumor is removed multiple secondary tumors survive and proliferate. Consequently, there exists an immediate and pressing need for techniques of eradicating secondary tumors that already exist.

Cancer cells that escape the primary tumor are usually carried in the venous and lymphatic circulation until they lodge in a downstream capillary bed or lymph node. However, only 1 in 10,000 of the cancer cells that escape the primary tumor survive to establish a secondary tumor. Successful cancer cells are those that find a favorable environment for survival and growth. The favorable environment include hormones and growth-promoting factors. Stimulating factors include local growth factors, hormones produced by the host, and autostimulating growth factors produced by the tumor cells themselves. Consequently, there is an immediate and pressing need for techniques capable preventing or inhibiting metastasis of cancer and the formation of secondary tumors.

Additionally, many other hyperproliferative disorders exist. Hyperproliferative disorders are caused by non-cancerous (i.e. non-neoplastic) cells that overproduce in response to a particular growth factor. Examples of such hyperproliferative disorders include diabetic retinopathy, psoriasis, endometriosis, macular degenerative disorders and benign growth disorders such as prostate enlargement and lipomas.

It is known that many new cancers are initiated, and existing cancers and hyperproliferative disorders stimulated, by growth factors that affect either the cancer cell itself or normal tissue around the cancer that facilitate survival of the cancer cell (i.e., angiogenesis factors). There is a direct correlation between the circulating level of certain growth factors and cancer proliferation. A potential method of treatment would be to regulate the level of circulating growth factors in a patient to prevent cancers initiation or recurrence and to reduce or eliminate existing cancers. What is needed, therefore, are compositions that remove the appropriate growth factors from circulation or inhibit the growth-promoting activity of growth factors.

SUMMARY OF THE INVENTION

The present invention generally involves methods and compositions for preventing or treating cancers. The present invention more particularly involves immunogenic growth factor-containing compositions which elicit the production of antibodies specific for growth factor when administered to a human or animal.

The present invention provides a method of vaccinating a human or animal against growth factors that are associated with specific cancer types and hyperproliferative disorders. Certain cancers are associated with only one growth factor and other cancers are regulated by growth factors. For example, certain T cell lymphomas produce the growth factor IL-2, which stimulates proliferation by autocrine action; other tumors produce factors that promote angiogenesis and stimulate growth of metastatic cancer lesions by inducing vascularization of tissue at the site of metastases.

Examples of growth factor-containing compositions include liposomes or vesicles having portions of growth factor, growth factor fragments, synthetic peptides of certain epitopes of growth factors, or modified growth factor fragments presented on their external surfaces. The above described compositions are useful as vaccines to induce autoimmunity against growth factors which otherwise are recognized as "self" by the immune system and are not naturally antigenic. The resulting circulating antibodies bind growth factor and thereby prevent the initiation of cancer proliferation, reduce existing cancer, or inhibit the spread of cancers.

The present invention also includes antibodies specific for growth factors. These antibodies are produced by and purified from humans or animals with strong immune systems, and injected into humans or animals with weak or non-functional immune systems in need of such circulating antibodies. Thus, according to the present invention, cancers are reduced or inhibited either by active immunization of an individual using antigenic growth factor-containing compositions, or by passive immunization via administering an antibody or a group of antibodies specific for growth factor epitopes. Additionally, patients are immunized with the growth factor composition prior to the initiation or recurrence after treatment of cancer.

Accordingly, it is an object of the present invention to provide methods and compositions for reducing cancer in a human or animal having cancer.

It is another object of the present invention to provide methods and compositions for preventing the occurrence or spread of cancer.

It is yet another object of the present invention to provide methods and compositions for vaccinating a human or animal against growth factor.

It is yet another object of the present invention to provide methods and compositions for passively immunizing a human or animal against growth factor.

Another object of the present invention is to provide growth factor-containing compositions that are antigenic and elicit an immune response against growth factor in humans or animals.

Yet another object of the present invention is to provide growth factor peptide fragments modified with antigenic moieties to increase an individual's response to growth factor and methods of use thereof.

It is yet another object of the present invention to provide growth factor peptide fragments and modified growth factor peptide fragments in liposomes.

It is still another object of the present invention to provide growth factor peptide fragment-containing compositions in combination with adjuvants to stimulate the immune response.

Another object of the present invention is to provide anti-growth factor antibodies useful for passively immunizing a human or animal against growth factor.

These and other objects, features and advantages of the present invention will become apparent after a review of the following detailed description of the disclosed embodiment and the appended claims.

Detailed Description of the Present Invention

The present invention comprises methods and compositions for preventing or reducing cancer and hyperproliferative disorders in a human or animal. The antigenic growth factor-containing compositions of the present invention include, but are not limited to, growth factor containing carriers, such as liposomes and vesicles, antigenic growth factor peptide fragments, antigenic growth factor peptide fragments combined with adjuvants, modified growth factor peptide fragments, modified growth factor peptide fragments combined with adjuvants, carriers containing growth factor peptide fragments, and carriers containing modified growth factor peptide fragments. Still further, the present invention includes antibodies directed against, and specific for growth factors.

As used herein, the term "growth factor" refers to polypeptide growth factors and polypeptide angiogenesis factors, and modified derivatives and peptide fragments thereof. Growth factor includes:

Fibroblast growth factor (FGF);
Interleukins 1-12 (IL-1$\alpha$, $\beta$, IL-2, IL-3, IL-4, IL-5, IL-6, IL-7, IL-8, IL-9, IL-10, IL-11, IL-12);
Kerotinocyte growth factor;
Colony stimulating factors such as, Granulocyte Colony Stimulating Factor (G-CSF), Macrophage Colony Stimulating Factor (M-CSF or CSF-1), and GM-CSF;
Epidermal Growth Factor (EGF);
Vascular Endothelial Growth Factor (VEGF, otherwise known as Vascular Permeability Factor);
Transforming Growth Factor $\alpha$ (TGF-$\alpha$);
Transforming Growth Factor $\beta_1$ through $\beta_5$ (TGF-$\beta$);
Schwann cell-derived Growth Factor;
Nerve Growth Factor (NGF);
Platelet-derived Growth Factor (PDGF);
Insulin-like Growth Factors 1 and 2 (IGF-1 and IGF-2);
Glial Growth Factor;
Tumor Necrosis Factor $\alpha$ and $\beta$ (TNF-$\alpha$, TNF-$\beta$);
Prolactin; and
Growth hormone.

Also as used herein, the term "immunogenic" refers to substances which elicit or enhance the production of antibodies, T-cells and other reactive immune cells directed against an endogenous growth factor and contribute to an immune response in humans or animals.

An individual may have circulating antibodies directed against endogenous growth factors yet the individual does not experience an immune response against the growth factor. Thus, the term "non-immunogenic" as used herein refers to endogenous growth factor in its native state which normally elicits no, or only minimal levels of, circulating antibodies, T-cells, or reactive immune cells, and which normally does not elicit in the individual an immune response against itself. An immune response occurs when an individual produces sufficient antibodies, T-cells and other reactive immune cells against administered growth factor compositions of the present invention to moderate or alleviate the cancer or hyperproliferative disorder to be treated.

The term "carrier" as used herein means a membranous structure in which growth factor can be incorporated, thereby presenting or exposing growth factor or part of the growth factor on the external surface of the carrier and rendering the growth factor-carrier composition antigenic for growth factor.

Further, the term "effective amount" refers to the amount of growth factor which, when administered to a human or animal, elicits an immune response, prevents cancer, causes a reduction in cancer or inhibits the spread and proliferation of cancer. The effective amount is readily determined by one of skill in the art following routine procedures.

For example, immunogenic growth factor compositions may be administered parenterally or orally in a range of approximately 1.0 $\mu$g to 1.0 mg per patient, though this range is not intended to be limiting. The actual amount of growth factor composition required to elicit an immune response will vary for each individual patient depending on the immunogenicity of the growth factor composition administered and on the immune response of the individual. Consequently, the specific amount administered to an individual will be determined by routine experimentation and based upon the training and experience of one skilled in the art.

The growth factor-containing compositions of the present invention are used to produce antibodies directed against portions of growth factor rendered immunogenic by their presentation in the carrier. Anti-growth factor antibodies are administered to individuals to passively immunize them against growth factor and thereby prevent the initiation of cancer growth, reduce existing cancer or inhibit the proliferation of cancer.

More specifically, the present invention encompasses growth factor inserted into membranous carriers so as to present on the carrier surface portions of growth factor. The growth factor normally is not immunogenic because it is recognized by the immune system as "self." However, inserting portions of growth factor into the surface of liposomes alters the presentation of the growth factor to the immune system, rendering it immunogenic.

Immunogenic growth factor-containing liposomes may be made by reconstituting liposomes in the presence of purified or partially purified growth factor. Additionally, growth factor peptide fragments may be reconstituted into liposomes. The present invention also includes growth factor and growth factor peptide fragments modified so as to increase their antigenicity. For example, antigenic moieties and adjuvants may be attached to or admixed with the growth factor. Examples of antigenic moieties and adjuvants include, but are not limited to, lipophilic muramyl dipeptide derivatives, nonionic block polymers, aluminum hydroxide or aluminum phosphate adjuvant, and mixtures thereof.

The present invention further encompasses growth factor fragments modified with hydrophobic moieties, such as palmitic acid, that facilitate insertion into the hydrophobic lipid bilayer of a carrier. Hydrophobic moieties of the present invention may be fatty acids, triglycerides and phospholipids wherein the fatty acid carbon back bones has at least 10 carbon atoms. Most preferable are lipophilic moieties having fatty acids with a carbon backbone of at least approximately 14 carbon atoms and up to approximately 24 carbon atoms. The most preferred hydrophobic moieties have a carbon backbone of at least 14 carbon atoms. Examples of hydrophobic moieties include, but are not limited to, palmitic acid, stearic acid, myristic acid, lauric acid, oleic acid, linoleic acid, and linolenic acid. The most preferred hydrophobic moiety is palmitic acid.

Immunogenic compositions containing growth factor, modified growth factor, and peptide fragments thereof are administered to a human or animal to induce immunity to growth factor. The immunized human or animal develops circulating antibodies against growth factor which bind to growth factor, thereby reducing or inactivating its ability to stimulate cancer cell proliferation.

Liposomes with growth factor inserted into the membrane, as well as other immunogenic compositions containing growth factor, also are used to produce a panel of monoclonal or polyclonal antibodies that are specific for growth factor. Antibodies are made by methods well known to those of ordinary skill in the art. Anti-growth factor antibodies bind growth factor when administered to individuals, reducing the effective circulating concentration of growth factor. Consequently, growth factor-dependent proliferation of cancer is prevented, reduced or inhibited.

The growth factor-containing compositions and anti-growth factor antibodies are administered to a human or animal by any appropriate means, preferably by injection. For example, growth factor reconstituted in liposomes is administered by subcutaneous injection. Whether internally produced or provided from external sources, the circulating anti-growth factor antibodies bind to growth factor and reduce or inactivate its ability to stimulate cancer cell proliferation.

Liposomes that can be used in the compositions of the present invention include those known to one skilled in the art. Any of the standard lipids useful for making liposomes may be used. Standard bilayer and multi-layer liposomes may be used to make compositions of the present invention. While any method of making liposomes known to one skilled in the art may be used, the most preferred liposomes are made according to the method of Alving et al., *Infect. Immun.* 60:2438–2444, 1992, hereby incorporated by reference. The liposome can optionally contain an adjuvant. A preferred adjuvant is detoxified lipid A, such as monophosphoryl or diphosphoryl lipid A.

When the vesicles are liposomes, the growth factor generally has a hydrophobic tail that inserts into the liposome membrane as it is formed. Additionally, growth factor can be modified to contain a hydrophobic tail so that the growth factor can be inserted into the liposome. For example, the growth factor gene is fused to a oligonucleotide sequence coding for a hydrophobic tail. The modified gene is inserted and expressed in an expression system, using methods known in the art, yielding a growth factor fusion protein having a hydrophobic tail. Alternatively, growth factor is exposed on the surface of previously formed liposomes by chemical attachment or electroinsertion.

When the vesicles are baculovirus-derived vesicles, recombinant growth factor is expressed on the membrane of the insect cell as a natural consequence of processing by the infected insect host cell. As with the liposome embodiment described above, growth factor may be modified so that the recombinantly expressed protein contains a hydrophobic portion to facilitate insertion into the vesicle membrane.

This invention is further illustrated by the following examples, which are not to be construed in any way as imposing limitations upon the scope thereof. On the contrary, it is to be clearly understood that various embodiments, modifications, and equivalents which, after reading the description herein, may suggest themselves to those skilled in the art are within the spirit of the present invention and are intended to be encompassed by the appended claims.

EXAMPLE I
Construction Of Growth Factor-Containing Recombinant Baculovirus

The baculovirus expression vector is constructed as described in Webb, N. R. et al. (1989) *Proc. Natl. Acad. Sci. USA* 86, 7731–7735, hereby incorporated by reference. A recombinant baculovirus containing cDNA encoding full-length growth factor under transcriptional regulation of the polyhedron promoter is produced by co-transfecting recombinant pAc-growth factor DNA with wild type *Autographa californica* nuclear polyhedrosis virus (*Ac*MNPV) DNA by calcium phosphate precipitation.

EXAMPLE II
Expression And Purification Of Growth Factor

The occlusion-negative viruses from Example I are plaque-purified and propagated in *Spodoptera frugiperda* 9 (*Sf*-9) cells. Infected *Sf*-9 cells are propagated in monolayers or suspension as described in Webb, N. R. et al. (1989) *Proc. Natl. Acad. Sci. USA* 86, 7731–7735. Briefly, *Sf*9 cells are cultured at 27° C. in TNMFH medium, described by Summers, M. D. and Smith, (1987) *A Manual of Methods for Baculovirus Expression Vectors and Insect Cell Culture Procedures* (Texas Agricultural Experiment Station, College Station, Tex.), Bull. 1555, supplemented with 10% v/v heat-inactivated fetal bovine serum. Extraction and purification of the recombinantly expressed growth factor is performed by standard methods.

EXAMPLE III
Preparation Of Growth Factor-Containing Liposomes

Purified growth factor is electroinserted (Mouneime, Y., et al., 1990, *Biochem.*, hereby incorporated by reference) or reconstituted into liposomes by standard methods known in the art. Incorporation of growth factors or fractions thereof into liposomes can include:

(a) rehydration of lyophilized liposomes of known lipid components in the presence of an aqueous solution of growth factor (or growth factor fragments) to make single- or multi-lamellar liposomes with growth factor contained in the lumen of the liposome or trapped in the aqueous layer between lipid membranes of the multi-lamellar vesicles;

(b) electroinsertion of the growth factor or fractions thereof into reconstituted liposomes, wherein the growth factor would reside in the lumen or between lipid membranes;

(c) reconstitution of prepared liposomes of known composition with lyophilized fragments of the growth factor, each fragment containing a hydrophobic tail which inserts directly into the liposome lipid bilayer such that the peptide fragment is exposed on the external surface of the liposome; and (d) any other method of reconstitution or combination of active reagents that results in the production of an immune response (humoral or cellular) directed to a growth factor, fractions thereof, or synthetic peptides that mimic the composition and activity of a growth factor.

EXAMPLE IV
Preparation Of Growth Factor-Containing Baculovirus Vesicles

Growth factor-containing vesicles are produced as follows. Insect-derived vesicles containing recombinant growth factor in their membranes are obtained using a baculovirus-infected insect cell. More particularly, Spodoptera frugiperda IPLB-*Sf*21-AE clonal isolate (designated *Sf*9) insect cells are cultured and infected with recombinant baculovirus containing a cDNA encoding the full-length growth factor as described more fully in Webb et al., *Proc. Natl. Acad. Sci.*, 86:7731–35 (1989), and in U.S. Pat. Nos. 4,745,051 and 4,879,236 both to Smith et al., which are hereby incorporated by reference. Approximately $0.8 \times 10^6$ *SF*9 cells are seeded into a 1 liter Spinner flask containing Excell media (JRH Scientific, Woodland, Calif. 95695). The cells are incubated at 27° C., 50% $O_2$ atmosphere. When the cells achieve a density of 3.5 to 4.0 million cells/ml, baculovirus containing recombinant growth factor is added at a multiplicity of 400–600 virus/cell to the media.

Vesicle production commences about 24 hours after baculovirus infection. Peak vesicle formation is achieved approximately 72 hours after initial baculovirus infection. Flask contents are collected and centrifuged at approximately 1200 rpm to remove cells and debris. The supernatant containing vesicles are collected and subjected to centrifugation on 50% Percoll containing 0.1M of sodium bicarbonate pH 8.3 at 20,000 RPM for 30 min using fixed-angle rotor. The double band is collected below an interphase between Percoll and cell culture medium and suspension is centrifuged in swing-bucket rotor at 20,000 RPM for 30 min. Two bands may be observed at the top and the bottom of the gradient with densities of 1.05 g/ml for vesicles and 1.06 g/ml for baculovirus particles. The vesicles have growth factor presented on their external surfaces and may be used for immunization. The vesicles are washed three times with 0.1M sodium bicarbonate pH 8.3 using centrifugation at 20,000 RPM for 20 min and resuspended in the same buffer.

EXAMPLE V
Immunization With Growth Factor-Containing Compositions

Immunogenic growth factor-containing compositions, either liposomes or baculovirus-derived vesicles, are injected into a human or animal at a dosage of 1–1000 μg per kg body weight. Antibody titers against growth factor are determined by ELISA, using the recombinant protein and horseradish peroxidase-conjugated goat anti-human or animal immunoglobulins, or other serologic techniques (sandwich ELISA), or biologic activity assays (such as neutralization of natural or synthetic cytokines or growth factor assays or competition assays) as presently exist or as developed specifically for individual growth factors. Booster injections are administered as needed to achieve levels of protective antibodies sufficient to reduce or neutralize the activity of growth factors in vivo. Neutralizing titers and appropriate antibody isotypes are determined in experimental animals challenged with appropriate cancer cells.

EXAMPLE VI
Preparation And Isolation Of Anti-Growth Factor Antibodies

Individuals with strong immune systems are immunized as described in Example V. After a high titer of anti-growth factor antibody has been achieved the IgG fraction is isolated from blood and is used to passively immunize an individual as described in Example VII below.

EXAMPLE VII
Passive Immunization

Anti-growth factor antibodies isolated from the species to be passively immunized are administered by intravenous injection as a dosage level of approximately 0.5–50 mg per kg body weight. Dosage and frequency of administration are determined in experimental animals challenged with different tumor types and are adjusted for the specific type of tumor and the particular individual being treated. Important considerations are the aggressiveness of the tumor, propensity for metastatic spread, target organ for metastases, target organ vascularization/availability of tissue access for antibodies, and the stage of tumor development. While it may be true that a standard regimen can be determined that will be universally protective, it may also be that effective therapy will be achieved only with individualized criterion based on tumor type.

While this invention has been described in specific detail with reference to the disclosed embodiments, it will be understood that many variations and modifications may be effected within the spirit and scope of the invention as described in the appended claims.

We claim:

1. A composition comprising,
   (a) a fibroblast growth factor or immunogenic peptide thereof; and
   (b) a liposome wherein the fibroblast growth factor or immunogenic peptide thereof is incorporated into the liposome such that the composition is immunogenic for the fibroblast growth factor or immunogenic peptide thereof when administered to a human or animal.

2. The composition of claim 1, further comprising an adjuvant.

3. The composition of claim 2, wherein the adjuvant is selected from the group consisting of lipophilic muramyl dipeptide derivatives, nonionic block polymers, aluminum hydroxide, aluminum phosphate and lipid A.

4. The composition of claim 2, wherein the adjuvant is lipid A.

5. The composition of claim 1, further comprising an immunogenic moiety attached to the growth factor or immunogenic peptide thereof.

6. The composition of claim 1, further comprising a hydrophobic moiety attached to the growth factor or immunogenic peptide thereof.

7. The composition of claim 6, wherein the hydrophobic moiety comprises at least one long chain fatty acid having at least 10 carbon atoms in the lipid backbone.

8. The composition of claim 6, wherein the hydrophobic moiety is selected from the group consisting of palmitic acid, stearic acid, myristic acid, lauric acid, oleic acid, linoleic acid, and linolenic acid.

9. A method for reducing an allogeneic cancer comprising administering to a human or animal an effective amount of an immunogenic fibroblast growth factor composition, wherein the composition comprises,
   (a) a fibroblast growth factor or immunogenic peptide thereof; and
   (b) a liposome wherein the fibroblast growth factor or immunogenic peptide thereof is incorporated into the liposome such that the composition is immunogenic for the fibroblast growth factor or immunogenic peptide thereof when administered to a human or animal.

10. The method of claim 9, wherein the composition further comprises an adjuvant.

11. The method of claim 9, wherein the adjuvant is selected from the group consisting of lipophilic muramyl dipeptide derivatives, nonionic block polymers, aluminum hydroxide, aluminum phosphate and lipid A.

12. The method of claim 9, wherein the composition further comprises an immunogenic moiety attached to the fibroblast growth factor or immunogenic peptide thereof.

13. The method of claim 9, further comprising a hydrophobic moiety attached to the growth factor or immunogenic peptide thereof.

14. The method of claim 13, wherein the hydrophobic moiety is selected from the group consisting of palmitic acid, stearic acid, myristic acid, lauric acid, oleic acid, linoleic acid, and linolenic acid.

15. A composition comprising,
   (a) a vascular endothelial growth factor or immunogenic peptide thereof; and
   (b) a liposome wherein the vascular endothelial growth factor or immunogenic peptide thereof is incorporated into the liposome such that the composition is immunogenic for the vascular endothelial growth factor or immunogenic peptide thereof when administered to a human or animal.

16. The composition of claim 15, further comprising an adjuvant.

17. The composition of claim 16, wherein the adjuvant is selected from the group consisting of lipophilic muramyl dipeptide derivatives, nonionic block polymers, aluminum hydroxide, aluminum phosphate and lipid A.

18. The composition of claim 15, further comprising an immunogenic moiety attached to the growth factor or immunogenic peptide thereof.

19. The composition of claim 15, further comprising a hydrophobic moiety attached to the growth factor or immunogenic peptide thereof.

20. The composition of claim 19, wherein the hydrophobic moiety comprises at least one long chain fatty acid having at least 10 carbon atoms in the lipid backbone.

21. The composition of claim 19, wherein the hydrophobic moiety is selected from the group consisting of palmitic acid, stearic acid, myristic acid, lauric acid, oleic acid, linoleic acid, and linolenic acid.

22. A method of treating an individual in need of an immune response to a growth factor comprising administering to a human or animal an effective amount of an immunogenic vascular endothelial growth factor composition, wherein the composition comprises,
   (a) a vascular endothelial growth factor or a peptide epitope thereof; and
   (b) a liposome wherein the vascular endothelial growth factor or immunogenic peptide thereof is incorporated into the liposome such that the composition is immunogenic for the vascular endothelial growth factor or immunogenic peptide thereof when administered to a human or animal.

23. The method of claim 22, wherein the composition further comprises an adjuvant.

24. The method of claim 22, wherein the adjuvant is selected from the group consisting of lipophilic muramyl dipeptide derivatives, nonionic block polymers, aluminum hydroxide, aluminum phosphate and lipid A.

25. The method of claim 22, wherein the composition further comprises an immunogenic moiety attached to the vascular endothelial growth factor or immunogenic peptide thereof.

26. The method of claim 22, further comprising a hydrophobic moiety attached to the vascular endothelial growth factor or immunogenic peptide thereof.

27. The method of claim 26, wherein the hydrophobic moiety is selected from the group consisting of palmitic acid, stearic acid, myristic acid, lauric acid, oleic acid, linoleic acid, and linolenic acid.

28. The composition of claim 1 wherein the fibroblast growth factor is conjugated to the liposome.

29. The composition of claim 1 wherein the fibroblast growth factor is encapsulated within the liposome.

30. The method of claim 9 wherein the fibroblast growth factor is conjugated to the liposome.

31. The method of claim 9 wherein the fibroblast growth factor is encapsulated within the liposome.

32. The composition of claim 15 wherein the vascular endothelial growth factor is conjugated to the liposome.

33. The composition of claim 15 wherein the vascular endothelial growth factor is encapsulated within the liposome.

34. The method of claim 22 wherein the vascular endothelial growth factor is conjugated to the liposome.

35. The method of claim 22 wherein the vascular endothelial growth factor is encapsulated within the liposome.

* * * * *